United States Patent
Vlad

(10) Patent No.: US 7,233,828 B2
(45) Date of Patent: Jun. 19, 2007

(54) SELF-CONTAINED ELECTROTHERAPY

(75) Inventor: Vladimir Vlad, Ames, IA (US)

(73) Assignee: Glycon Technologies, L.L.C., Ames, IA (US)

( * ) Notice: Subject to any disclaimer, the term of this patent is extended or adjusted under 35 U.S.C. 154(b) by 203 days.

(21) Appl. No.: 11/071,688

(22) Filed: Mar. 3, 2005

(65) Prior Publication Data

US 2005/0197671 A1 Sep. 8, 2005

Related U.S. Application Data

(60) Provisional application No. 60/549,586, filed on Mar. 3, 2004.

(51) Int. Cl.
*A61N 1/00* (2006.01)

(52) U.S. Cl. .......... 607/148; 607/35; 607/144; 607/149; 310/326; 405/186

(58) Field of Classification Search .......... 607/2, 607/35, 115, 144, 148, 15, 149; 600/15; 2/2.15; 405/185, 186
See application file for complete search history.

(56) References Cited

U.S. PATENT DOCUMENTS

| | | | | |
|---|---|---|---|---|
| 1,006,415 A | * | 10/1911 | Stubling et al. ........... 600/13 |
| 4,509,527 A | | 4/1985 | Fraden |
| 4,729,377 A | * | 3/1988 | Granek et al. ........... 600/393 |
| 4,761,005 A | | 8/1988 | French et al. |
| 4,823,810 A | | 4/1989 | Dervieux |
| 5,072,035 A | | 12/1991 | Chen et al. |
| 5,158,039 A | * | 10/1992 | Clark ........... 119/712 |
| 5,203,349 A | | 4/1993 | Kogan |
| 5,496,356 A | | 3/1996 | Hudz |
| 5,553,626 A | * | 9/1996 | Burger et al. ........... 600/590 |
| 5,787,525 A | | 8/1998 | Sugihara et al. |
| 5,928,784 A | | 7/1999 | Sugihara et al. |
| 6,032,530 A | | 3/2000 | Hock |
| 6,120,531 A | * | 9/2000 | Zhou et al. ........... 607/111 |
| 6,198,204 B1 | * | 3/2001 | Pottenger ........... 310/326 |
| 6,438,428 B1 | * | 8/2002 | Axelgaard et al. ........... 607/152 |
| 6,602,544 B2 | | 8/2003 | Piselli |

(Continued)

FOREIGN PATENT DOCUMENTS

EP  0 847 773 A2  6/1998

(Continued)

OTHER PUBLICATIONS

Advanced Cerametrics Incorporated, Advanced Materials Technology Company "Piezoelectric Ceramic Fibers", pp. 1-10.

(Continued)

*Primary Examiner*—Robert E. Pezzuto
*Assistant Examiner*—Brian T. Gedeon
(74) *Attorney, Agent, or Firm*—McKee, Voorhees & Sease, P.L.C.

(57) ABSTRACT

A device for applying a therapeutic electrical field to a user's body includes an electroactive material shaped for application to a user body to provide a therapeutic electric field in response to pressure applied to the electroactive material and one or more electrodes integrated into the electroactive material and disposed along an inner surface of the electroactive material for delivering the therapeutic electric field to the user's body.

15 Claims, 4 Drawing Sheets

U.S. PATENT DOCUMENTS

| | | | |
|---|---|---|---|
| 6,607,500 B2 * | 8/2003 | Da Silva et al. | 602/2 |
| 6,694,185 B2 * | 2/2004 | Orton | 607/2 |
| 6,788,978 B2 * | 9/2004 | Vesnaver | 607/2 |
| 6,809,462 B2 * | 10/2004 | Pelrine et al. | 310/319 |
| 2003/0045195 A1 | 3/2003 | Piselli | |
| 2003/0186323 A1 | 10/2003 | Vogel et al. | |
| 2003/0233694 A1 * | 12/2003 | Wescombe-Down | 2/2.15 |
| 2005/0055061 A1 * | 3/2005 | Holzer | 607/35 |
| 2006/0122544 A1 * | 6/2006 | Ciluffo | 601/15 |
| 2006/0211934 A1 * | 9/2006 | Hassonjee et al. | 600/372 |

FOREIGN PATENT DOCUMENTS

| | | |
|---|---|---|
| EP | 0 847 773 A3 | 6/1998 |
| GB | 1 306 023 | 2/1973 |
| GB | 2 190 840 A | 12/1987 |

OTHER PUBLICATIONS www.nemowetsuit.com/technical_detail Nemo Newsletter "How to make a SCUBA diving westsuit from neoprene", Nemo Bali Wetsuit 2003/2004, pp. 1-4.

www.simolexrubber.com/html/cord_04.htmll Simolex Rubber Corporation, Simotex—Cord, Feb. 2004, 1 page.

www.sharkshield.co.za/products.html "Products" Feb. 2004, 6 pages.

www.bodi-tek.co.uk.v2/selotens/html Bodi-Tek Solo Tens—1 page.

www.ceramicbulletin.org Focus on Electronics "Applications, Markets Expand for Piezoelectric Ceramics", Sep. 2000 3 pages.

Phillips, James R. "Piezoelectric Technology Primer" 17 pages.

"Discussion of Principles" Mar. 3, 2004—2 pages.

* cited by examiner

SELF-CONTAINED ELECTROTHERAPY

PRIORITY STATEMENT

This application claims priority to U.S. Provisional Application No. 60/549,586 filed Mar. 3, 2004, hereby incorporated by reference in its entirety.

BACKGROUND OF THE INVENTION

1. Field of the Invention

The present invention relates to apparatus and methods integrating into clothing or articles worn or attached to a body, components which produce electrical energy based on mechanical strain on, movement of, or pressure on the components, making the electrical energy available for therapeutic purposes.

2. Problems in the Art

It has been proven that electrical energy can have therapeutic effect on human or animal tissue, muscles, and other physiological areas. There are a variety of methods and devices on the market that use this technique. For example, what is known as a TENS unit or device converts electrical energy from an external alternating current (AC) source or a battery into an electrical field that is applied to an injured or targeted portion of the body.

One problem with known devices and systems is they require an external or battery electrical power source. This usually means either limited mobility during treatment or added weight and bulk, which can be counterproductive or cumbersome for the user. Furthermore, most devices, including TENS devices, require electrodes to be adhesively placed on a targeted location of the body. Most times, the electrodes then must be hard-wired to a control unit. This is cumbersome to install and wear. It requires immobilization of the user to place the electrodes or remove them.

Many existing devices are also relatively expensive, and require close monitoring or even operation by health care professionals.

Another problem with using known devices and systems is in prescribing an appropriate treatment for a particular condition. In particular, some level of treatment may be therapeutic, but too much or too little may not be. Even a trained health care professional cannot adequately address this issue because they cannot predict with any amount of certainty how much activity a patient may be involved in and therefore how much therapy is appropriate.

There is a real need in this area for improvement. For example, there is a real need for technology that utilizes the benefits of electrical fields for therapeutic purposes, but with less constrictions on mobility of the user during treatment. There is also a need for a more efficient and economical method for administering such therapy.

SUMMARY OF THE INVENTION

Therefore, it is a primary object, feature, or advantage of the present invention to improve upon the state of the art.

It is a further object, feature, or advantage of the present invention to administer therapeutic levels of electric field treatment.

A still further object, feature or advantage of the present invention is to administer appropriate electrical field treatments.

Another object, feature, or advantage of the present invention is to provide a means for therapy that is convenient for users.

Yet another object, feature, or advantage of the present invention is to provide a means for electric field treatment that relates movement to the amount or intensity of treatment.

A further object, feature, or advantage of the present invention is to provide for an electrical field treatment that does not require immobilization of the user.

A still further object, feature, or advantage of the present invention is to provide for an electrical field treatment that does not require an external source of power such as batteries or AC line voltage.

Another object, feature, or advantage of the present invention is to provide for a device for administering treatment that is portable.

Yet another object, feature, or advantage of the present invention is to provide for a device for administering treatment that is not bulky, heavy, or cumbersome.

A further object, feature, or advantage of the present invention is to provide for a device for administering treatment that does not substantially interfere with mobility of the patient or user.

A still further object, feature, or advantage of the present invention is to provide for a device for administering treatment that is economical.

Another object, feature, or advantage of the present invention is to provide for a device for administering treatment that is durable and relatively long lasting.

Yet another object, feature, or advantage of the present invention is to provide for a device for administering treatment that provides on the user an electrical energy generator, which avoids having limited operating times associated with batteries with no renewable source.

A further object, feature, or advantage of the present invention is to provide for a device for administering treatment that does not require time and resources to adhere electrodes to the body.

A still further object, feature, or advantage of the present invention is to provide a device for administering therapeutic electrical treatment that is self-regulating.

Another object, feature, or advantage of the present invention is to provide a device for administering therapeutic electrical treatment that can provide therapy during exercise, including during competitive athletics.

One or more of these and/or other objects, features, or advantages of the present invention will become apparent from the specification and claims that follow. According to one embodiment of the present invention, a device for applying a therapeutic electrical field to a user's body includes an electroactive material shaped for application to a user body to provide a therapeutic electric field in response to pressure applied to the electroactive material and one or more electrodes integrated into the electroactive material and disposed along an inner surface of the electroactive material for delivering the therapeutic electric field to the user's body. The device may be shaped as a sleeve or may be shaped in other configurations. The electroactive material can be a pressure-activated conductive rubber or another type of pressure-activated elastomer. Alternatively, the electroactive material may include a number of electroactive fibers.

According to another aspect of the invention a method of therapy is provided. The method of therapy includes positioning a device for applying a therapeutic electrical field on user's body and applying pressure to the device. The device includes an electroactive material shaped for application to a user body to provide a therapeutic electric field in response to pressure applied to the electroactive material, and one or more electrodes integrated into the electroactive material and disposed along an inner surface of the electroactive material for delivering the therapeutic electric field to the user's body. Pressure can be applied by body movement.

Figure 1:
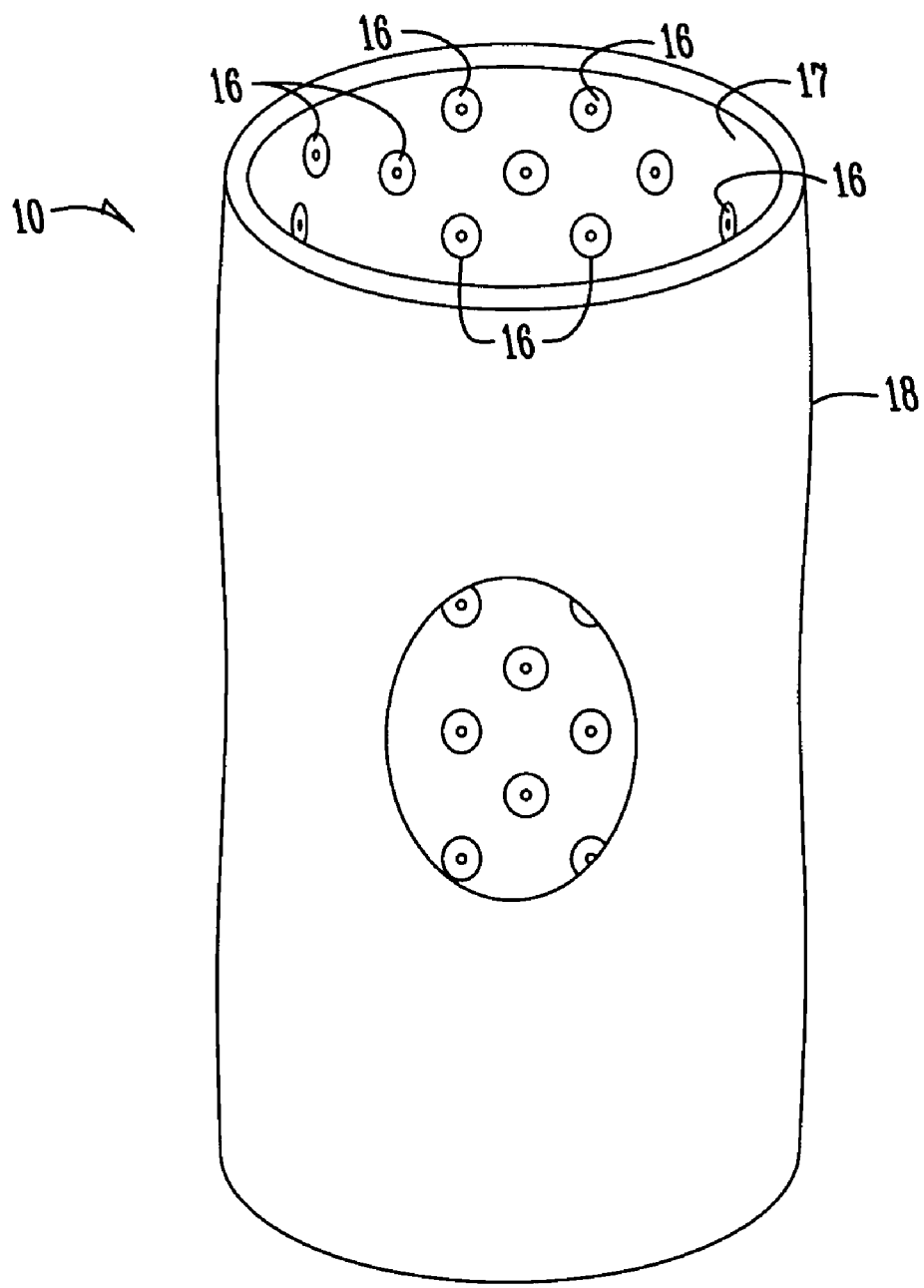
FIG. 1 is a simplified side elevation diagrammatic illustration of a knee guard 10 that creates therapeutic electrical fields when the user of the knee guard moves.

DESCRIPTION OF EXEMPLARY
EMBODIMENTS OF THE INVENTION

To obtain a better understanding of the invention, a description of a few exemplary embodiments will now be set forth. The exemplary embodiments are illustrative only and not by way of limitation to the invention. Reference will be taken from time to time to the above-identified drawings. Reference numbers and letters will be used to indicate certain parts and locations in the drawings. The same reference numbers will be used to indicate the same parts or locations throughout the drawings unless otherwise indicated.

FIG. 1 illustrates one embodiment of a physiotherapeutic sleeve of the present invention. The physiotherapeutic sleeve shown is a knee guard 10. The knee guard 10 is of conventional configuration except as discussed below. It substantially elastically surrounds the knee area of the user, leaving, between opposite open ends for insertion of the leg, an intermediate opening in the side for the knee cap. A similar structure exists for elbows. The physiotherapeutic device of the present invention can take other shapes or configurations as may be appropriate for a particular treatment, including, but not limited to treatment with respect to wrists, ankles, back, or other body parts.

In a preferred embodiment, a pressure-activated conductive rubber is used such as that described in U.S. Provisional Patent Application No. 60/646,265 filed Jan. 24, 2005, herein incorporated by reference in its entirety. In such an application, the physiotherapeutic sleeve is formed form an appropriate pressure-activated conductive rubber (although other elastomers may be used). The knee guard 10 has an inside surface 17 and an outside surface 18. There are a plurality of conductive (preferably metallic) eyelet electrodes 16 distributed throughout the inside surface 17. The integrated electrodes 16 receive electrical impulses directly proportional with the pressure and/or time applied on the knee guard. Thus, based on the movement of a user and the amount of movement, electrical impulses are applied. For example, increased movement will result in an increase in electrical therapy. This can be a highly advantageous result as it allows the therapy provided by the device to be self-regulating.

Figure 2:
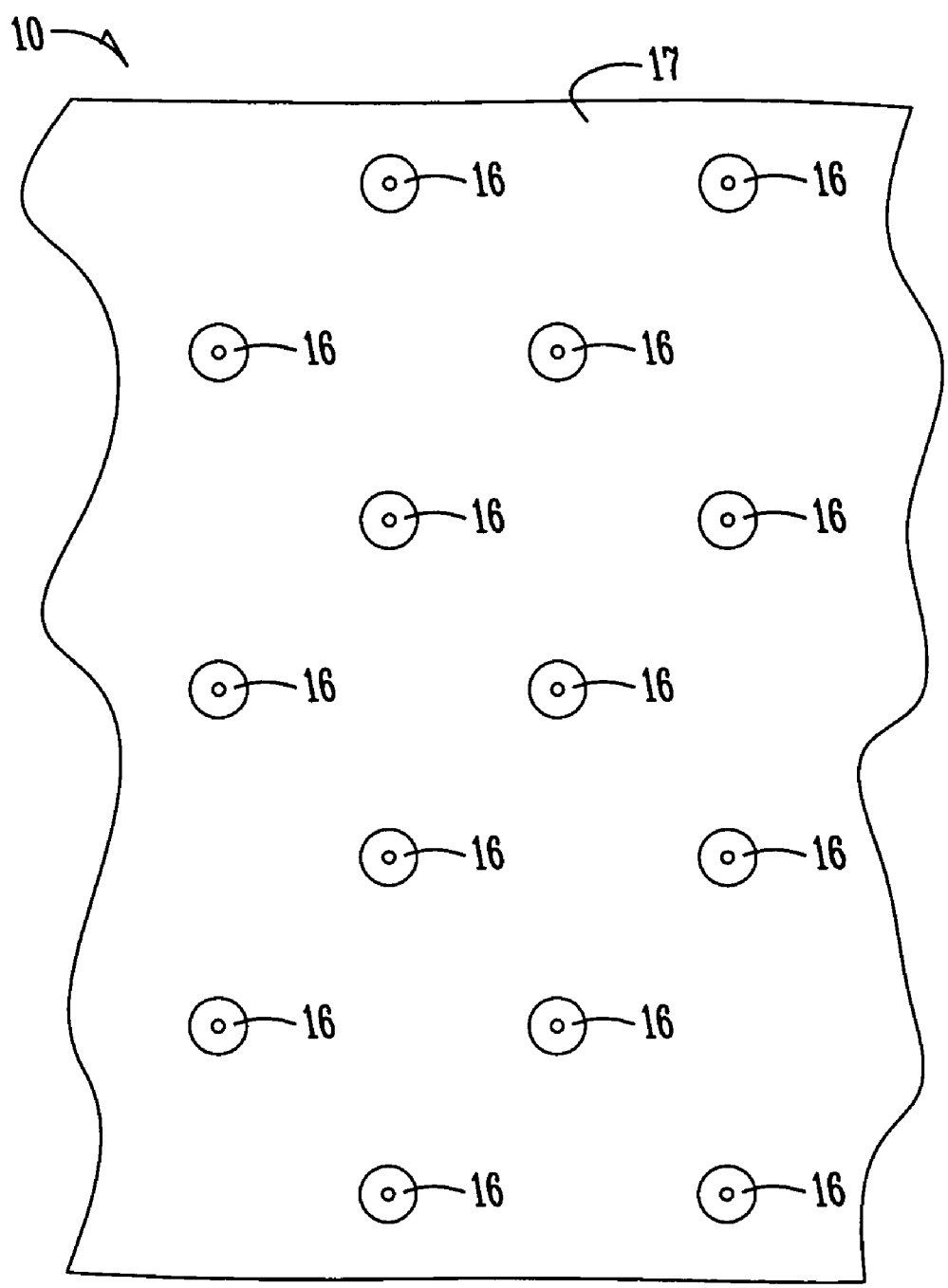
FIG. 2 is a sectional view of a knee guard 10 like in FIG. 1, illustrating placement of electrodes on the interior portion of a physiotherapeutic sleeve 10.

Note that the electrodes can be positioned in any number of arrangements as may be appropriate for a particular treatment, or the electrodes can merely be positioned throughout the physiotherapeutic device. FIG. 2 illustrates one example of a configuration.

It is preferred that the material used in the physiotherapeutic device can be formed with a formed form an appropriate pressure-activated conductive rubber prepared through sonic homogenization. One method of forming an appropriate pressure-activated conductive rubber is to sonically homogenize a mixture of an electroactive powder and a conductive rubber. One example of an appropriate conductive rubber is ZOFLEX ZL 60.1 pressure-activated conductive rubber. Ultrasound is applied to a mixture (such as a 1:1 mixture) of an electroactive powder such as a Terfernol-D ($Tb_3$ $Dy_7$ $F_e$) powder, or EC-65, EC-97 or EC-98 electroceramic powders. The ultrasound frequency can be 20 KHz. The mixture is polarized through application of a DC voltage to produce a closed cell formation. The material can be further polarized under high compressed pressure. Instead of a conductive rubber, other types of conductive elastomers can be used.

Figure 3:
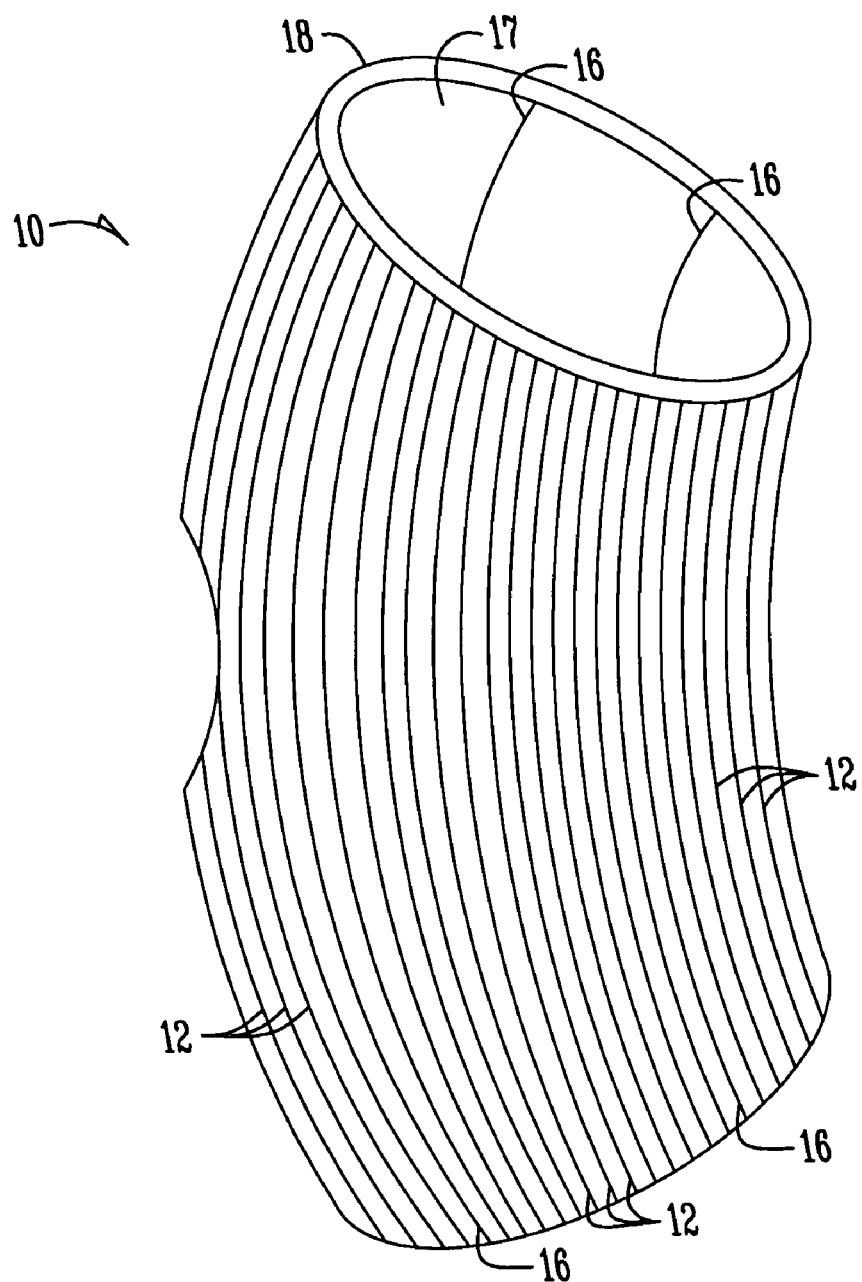
FIG. 3 is a simplified side elevation diagrammatic illustration of an alternative embodiment of a knee guard 10 adapted to create therapeutic electrical fields.

According to another embodiment of the present invention, electroactive fibers are embedded in a fabric-type material. The knee guard 10 of FIG. 3 differs from conventional knee guards in that, as illustrated at FIG. 3, it includes a plurality of PZT fibers or strips 12 integrated into the fabric longitudinally along the knee guard from end to end. By integrated it is meant operatively installed to the knee guard. Some examples, not exclusive, are either physically incorporated into the fabric or material, or otherwise attached to the outer or inner surface of the material. While fibers or strips 12 might be removable, it is believed preferable to make them permanently integrated with the material.

In this example, fibers 12 are Piezoelectric Ceramic Fibers PZT and are incorporated as strips into the knee guard material. Fibers 12 are preferably themselves at least somewhat elastic or elastomeric, such that they bend and twist with movement of the knee. Thus, incorporation of fibers 12 into knee guard 10 does not substantially restrict mobility of the user compared to just a conventional knee guard.

One example of fibers 12 are PZT fibers manufactured by Viscose Suspension Spinning Process (VSSP) method with cross-sections of 10 to 250 μm.

The fibers can be made in a form that is like other fabric threads. It therefore can be integrated into fabrics and materials of clothing, including but not limited to knee guards, elastic wraps, and other apparatus or clothing, by known manufacturing methods. The fibers are believed robust enough to take conventional manufacturing techniques for these types of materials without material damage to their function or efficacy. The fibers could replace normal fibers or be added to normal fibers or materials. They can be placed in just one portion of clothing, or in a plurality of positions. Different sets could be placed in different positions. It may be possible to have different sets of fibers in the same location.

The fibers could also be strips or other forms. They have electroactive or piezoelectric type properties. They output a voltage when subjected to some mechanical force.

A piezoelectric material is defined as a material that develops an electric charge when pressed or subjected to a force. PE materials transform mechanical work input into electrical output and vice versa. A simple piezoelectric accelerometer consists of a disk-like base of PE material connected to a proof mass. The base is secured to the moving body and electrodes are connected on either side of the disk. When the body accelerates, the proof mass exerts a force on the PE disk and a charge builds up across the electrodes.

Piezoelectric accelerometers are called active devices since they generate their own signals, and theoretically do not need to be powered.

The piezoelectric property of ceramics like PZT does not arise simply from its chemical composition. In addition to having the proper formulation, the piezoceramic must be subjected to a high electric field for a short period of time to force the randomly oriented micro-dipoles into alignment. This alignment by application of high voltage is called "poling". At a later time, if an electric field is applied in the opposite direction it exerts a "dislodging stress" on the micro-dipoles. Low level applied fields result in no permanent change in the polarization (it bounces back upon removal). Medium fields result in partial degradation of the polarization (with partial loss of properties). High applied fields result in repolarization in the opposite direction.

The most common method is to make a conductive bond between a metal substrate and the piezo part. Then one electrical lead is attached to the substrate, and one to the outward face of the piezoceramic sheet. In cases where a conductive bond is not possible (i.e. when the substrate is glass or plastic), a wire must be soldered to the "down" side of the ceramic at some location and a corresponding 'dish', 'cutout', or 'overhang' must be used to allow room for the wire when bonding the piezo sheet to the substrate.

Many piezoceramic parts come with a thin (~3000 Angstrom units) metallic electrode already on the ceramic. Wire leads can be soldered (use ordinary 60/40 resin core solder) anywhere on the electrode to suit the application/experiment. Most PSI ceramics have thin nickel electrodes and require the use of an additional liquid flux for uniform results.

Sets of fibers 12 could be selected and associated with one or more electrodes 16. For example, in FIG. 1, four electrodes 16 are extended longitudinally along guard 10 basically parallel with fibers 12. Selected sets of PZT fibers 12 can be operatively connected to an epoxy multilayer transducer (not shown) that harvest the electrical energy or charge of the selected set of fibers 12. In a way, the transducers are like the metal substrate and lead on opposite sides of a monolithic piezoelectric member. Each transducer at opposite ends of the fibers collects the polarized charge that builds up towards its end of the set of fibers. It can be electrically connected to another component; here an electrode. Thus, the transducers (e.g. operatively connected to opposite ends or opposite polarities of a set of fibers 12), provide two electrical connections of opposite polarity to the plurality of fibers 12 between them. The transducers therefore allow what some call the "harvesting" of electrical energy from multiple PZT fibers. By appropriate electrical connection (e.g. hardwiring), a transducers can be electrically connected to an electrode 16. By appropriate selection and connection, certain electrodes 16 at a given moment in time can be of one polarity or charge (e.g. +) and certain electrodes 16 the opposite polarity or charge (e.g. −). By design, electrodes 16 of opposite charge on opposite sides of knee guard 10 would create an electrical or electromagnetic field between them, and thus through the user's knee. Thus, using the electrical generator integrated in the knee guard 10, an electric or electromagnetic field for therapeutic purposes is created for the wearer of guard 10.

In one example, fibers 12 could be operatively connected to an epoxy multilayer transducer which harvests or collects the electrical energy generated by fibers 12 and transfers the harvested electrical energy to an elongated elastic electrode (diagrammatically illustrated at reference numeral 16) that are also integrated into knee guard 10 along its length.

Each electrode 16 can be opposite in polarity relative to its adjacent electrodes 16 or opposite electrode 16. When electrical energy is harvested from fibers 12 by transducer 14, it is transferred to electrodes 16. Electrical fields are set up between electrodes of opposite polarity. Electrical fields 18 are basically radially across the entire cross section of knee guard 10 and all along its length. Therefore therapeutical application of electrical fields to the entire user's knee area is accomplished, not just between relatively small electrodes adhered to the leg, like with many TENS units.

The transducers can take different forms. The multilayer example could have four layers of epoxy transducers electrically connected to an elastic electrode. These transducers have long lives (e.g. $200 \times 10^6$ cycles without properties diminishing).

The electrodes can be silicone strips that can be integrated into or on the inner or outer side of knee guard 10.

Figure 4:
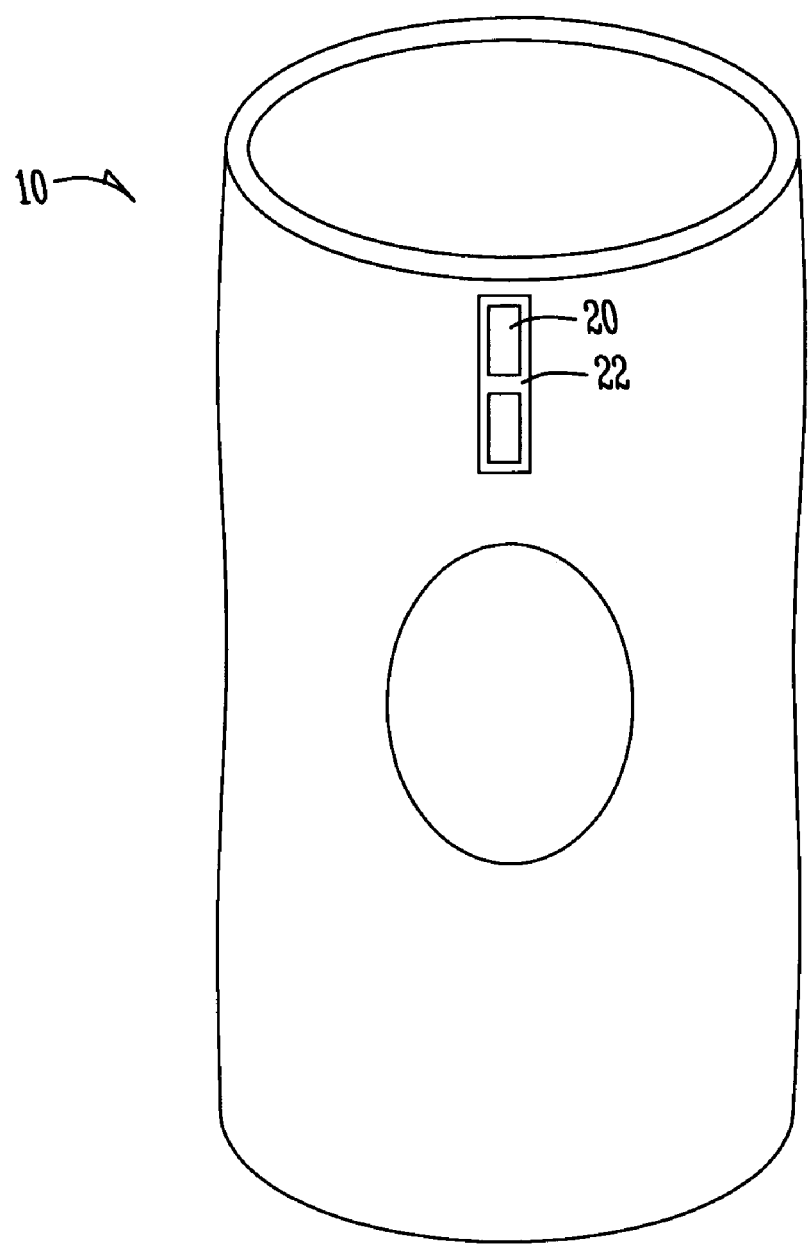
FIG. 4 is a simplified front elevation view of one embodiment of the invention illustrating optional control components.

Pressure, mechanical strain, or motion on fibers 12, usually by movement of the user causing bending of the knee, will generate a protective elliptic electric field via electrodes 16 (e.g. elastic conductive silicon rubber members). With a manually operated electronic switch (see diagrammatic depiction at reference number 20 in FIG. 4) incorporated, for example, into or on the knee guard, the whole device can be activated or deactivated by the user whenever desired. An electric field is always associated with the presence of electric charges. It fills the space around the charge and is the mechanism of interaction between charges. A test particle with small known charge (Q) placed near a charge concentration will experience an accelerating force (F) due to the field. The value of the electric field (E) at that location is the ratio F/Q (a vector).

Thus, as can be seen, when guard 10 is worn and electrical energy generated in fibers 12, the user's knee would be substantially enveloped in electrical fields. As can be appreciated, the number of fields can be designed by the number and configuration of electrodes used. The PZT fibers with transducers and electrodes can be incorporated into at least a portion of guard 10.

In this example, the electrical energy is collected into opposite charges at electrodes 16. In this example, elastic conductive silicon rubber electrodes 16 and elastic PZT strips 12 are alternated longitudinally around knee guard 10.

The stretch/twist/pressure and motion that arises when the user moves his/her leg will generate an electric field into the injured joint or muscle similar to that applied by conventional electrotherapy pads, but more comprehensively and in a less cumbersome manner. The device eliminates the necessity of any additional source of energy (batteries or AC) and is fully portable during exercises.

The system of the present invention is less bulky than most existing therapeutic systems, does not require a battery, is less restrictive and cumbersome, and is believed to be less costly. It improves mobility and provides a self-contained, continuous renewable energy generating source. Nothing must be carried in the user's hands or strapped to a user's waist. In addition, the therapeutic system of the present invention can be self-regulating to provide an appropriate level of therapy. Further it is contemplated that the a physiotherapeutic sleeve can be worn during physical activity, including during exercise or even during competitive sports.

The preceding description of exemplary embodiments is for illustrative purposes only, and not for limitation of the invention. Variations obvious to those skilled in the art are included with the claimed invention. Variations to the preceding embodiments, including changes in dimensions and configurations, structures, and specific methodology are possible. Also, optional features can be added to the basic configuration.

Some specific examples of options or alternatives are as follows. An electromagnetic field sensor may optionally be incorporated with a regulator switch, so the wavelength of the electrotherapy applied will be focused on the weak points and in direct proportion with the tissues' damage. For example, a bio-feedback or other sensor of bioelectric activity of the user could be added. Its output could be operatively connected to circuitry that would instruct when and how much electrical energy should be applied to the targeted portion of the user's body. A simple circuitry (e.g. small programmable microprocessor) could turn on the electrical fields and/or adjust intensity based on bio feed back from such a sensor. Stated differently, by monitoring the bioelectrical field of the user's body, the circuit could determine intensity of the therapeutic energy applied. Such biofeedback sensors are available commercially.

An example of such a bioelectrical field sensor is described in literature regarding VEGA (the Slovak Grant Agency for Science), a scanner system that would monitor biological properties of the user and feed back information that could, by appropriate design or programming, be used to automatically adjust the intensity, duration, or other aspects of the electric field generated by knee guard 10. An inertial sensor, such as are commercially available, or some other commercially available device, could sense the amount of movement of the user. It could be used, for example, to automatically increase intensity of the electricity output by the suit (e.g. increase magnitude of electric fields for shark repellant) if it senses reduced user movement. It could do this by some circuitry to increase the field, or possibly by tapping into stored energy in a battery just in those times. When the user is moving more robustly, it could sense the same and reduce the amount of energy used (or divert excess into a battery for later use). It might also simply be hooked to some type of alarm or notification device to tell the user to increase movement to maintain a certain level of therapeutic effect.

It is possible to use a memory chip and related circuitry to analyze the user's sensed bioelectrical field and regulate the magnitude or frequency of the electric fields applied to the user. The circuit could essentially work autonomously and be self-selective in its treatment. It is possible a regulatory circuit with a manual control (see FIG. 2, reference number 22) could be integrated or added to knee guard 10 to allow the user or another person to manually adjust or modulate the electrical or electromagnetic fields produced by guard 10. But, as mentioned, other circuitry could be designed to automatically control the same.

A possible application would be to incorporate the fibers 12, transducer 14, and electrodes 16 into a portion or substantial portion of a lycra top or bottom, or full body suit. The electric fields, when generated, could have not only healing effect but possibly energizing effect on the user, if not injured but only tired.

The invention claimed is:

1. A device for applying a therapeutic electrical field to a user's body comprising:

an electroactive material shaped for application to a user body to provide a therapeutic electric field in response to pressure applied to the electroactive material;

one or more electrodes integrated into the electroactive material and disposed along an inner surface of the electroactive material for delivering the therapeutic electric field to the user's body; and wherein the electroactive material is comprised of a plurality of electroactive fibers.

2. The device of claim 1 wherein the electroactive material is shaped as a sleeve.

3. The device of claim 1 wherein the electroactive material is a pressure-activated conductive rubber.

4. The device of claim 1 wherein the electroactive material is a pressure-activated conductive elastomer.

5. The device of claim 1 wherein the electroactive fibers are oriented to have opposite ends of opposite electrical polarity.

6. The device of claim 1 wherein the electroactive fibers and one or more electrodes are elastomeric.

7. The device of claim 1 wherein the plurality of fibers are piezoelectric fibers.

8. The device of claim 1 wherein the one or more electrodes are elastic silicone pads.

9. The device of claim 1 further comprising a transducer operatively connected to the electroactive material and the at least one electrode, the transducer adapted to harvest electrical energy from the plurality of electroactive material and transfer it to the at least one electrode to create an electric field.

10. A method of therapy, comprising:

positioning a device for applying a therapeutic electrical field on user's body, the device comprising (a) an electroactive material comprised of electroactive fibers and shaped for application to a user body to provide a therapeutic electric field in response to pressure applied to the electroactive material (b) one or more electrodes integrated into the electroactive material and disposed along an inner surface of the electroactive material for delivering the therapeutic electric field to the user's body; and applying pressure to the device.

11. The method of claim 10 wherein the step of applying pressure to the device is moving the user's body to thereby apply pressure to the device.

12. The method of claim 10 wherein the moving is associated with exercise.

13. The method of claim 10 wherein the therapeutic electrical field has one or more properties determined by the pressure.

14. The method of claim 13 wherein the one or more properties include magnitude of the therapeutic electrical field.

15. The method of claim 13 wherein the one or more properties include location of the therapeutic field.

* * * * *